United States Patent
Bröll et al.

(10) Patent No.: US 11,027,245 B1
(45) Date of Patent: Jun. 8, 2021

(54) PROCESS FOR CONTINUOUS DISSOLUTION OF A SOLID IN A REACTION MEDIUM

(71) Applicant: Evonik Operations GmbH, Essen (DE)

(72) Inventors: Dirk Bröll, Langen (DE); Thorsten Noll, Mainz (DE)

(73) Assignee: Evonik Operations GmbH, Essen (DE)

( * ) Notice: Subject to any disclaimer, the term of this patent is extended or adjusted under 35 U.S.C. 154(b) by 39 days.

(21) Appl. No.: 16/628,092

(22) PCT Filed: Jun. 28, 2018

(86) PCT No.: PCT/EP2018/067357
§ 371 (c)(1),
(2) Date: Jan. 2, 2020

(87) PCT Pub. No.: WO2019/007786
PCT Pub. Date: Jan. 10, 2019

(30) Foreign Application Priority Data

Jul. 5, 2017 (DE) .................... 10 2017 211 435.5

(51) Int. Cl.
*B01F 1/00* (2006.01)
*B01J 8/00* (2006.01)
(Continued)

(52) U.S. Cl.
CPC ............ *B01F 1/0038* (2013.01); *B01D 3/143* (2013.01); *B01F 1/0005* (2013.01); *B01J 8/0242* (2013.01);
(Continued)

(58) Field of Classification Search
CPC .. B01D 3/00; B01D 3/14; B01D 3/143; B01F 1/00; B01F 1/0005; B01F 1/0038;
(Continued)

(56) References Cited

U.S. PATENT DOCUMENTS

| 5,322,960 A | 6/1994 | Sakamoto et al. |
| 7,714,165 B2 | 5/2010 | Broell et al. |

(Continued)

FOREIGN PATENT DOCUMENTS

DE 102006029318 B3 * 10/2007 ............. C07C 51/56

OTHER PUBLICATIONS

U.S. Appl. No. 12/295,323, filed May 11, 2010, U.S. Pat. No. 7,714,165, Broell et al.

(Continued)

*Primary Examiner* — Natasha E Young
(74) *Attorney, Agent, or Firm* — Grüneberg and Myers PLLC (57) ABSTRACT

A process for continuous dissolution of a solid in a reaction medium includes: (a) providing a liquid by withdrawal of a portion of the reaction medium from a first reaction vessel; (b) contacting the liquid provided in (a) with the solid in a second reaction vessel to form a solution of the solid; and (c) recycling the solution formed in step b) into the first reaction vessel. The solid in the second reaction vessel is present in the form of a fixed bed which is traversed by the liquid.

17 Claims, 4 Drawing Sheets

(51) Int. Cl.
    *B01J 8/02*     (2006.01)
    *B01J 19/00*     (2006.01)
    *B01J 19/24*     (2006.01)
    *B01D 3/14*     (2006.01)
    *C07C 51/573*     (2006.01)
    *C07C 57/04*     (2006.01)
    *C07D 279/20*     (2006.01)

(52) U.S. Cl.
    CPC .......... *B01J 8/0278* (2013.01); *C07C 51/573* (2013.01); *B01J 2219/00038* (2013.01); *C07C 57/04* (2013.01); *C07D 279/20* (2013.01)

(58) Field of Classification Search
    CPC ..... B01J 8/00; B01J 8/02; B01J 8/0242; B01J 8/0278; B01J 19/00; B01J 19/24; B01J 2219/00; B01J 2219/00002; B01J 2219/00027; B01J 2219/00038; B01J 2219/24; C07D 279/00; C07D 279/10; C07D 279/14; C07D 279/18; C07D 279/20; C07C 51/00; C07C 51/54; C07C 51/573; C07C 57/00; C07C 57/02; C07C 57/03; C07C 57/04
See application file for complete search history.

(56) References Cited

U.S. PATENT DOCUMENTS

| | | |
|---|---|---|
| 8,084,640 B2 | 12/2011 | Broell et al. |
| 8,337,671 B2 | 12/2012 | Broell et al. |
| 2005/0143604 A1 | 6/2005 | Hammon et al. |
| 2009/0118533 A1 | 5/2009 | Broell et al. |
| 2009/0234161 A1 | 9/2009 | Paul |
| 2010/0069666 A1 | 3/2010 | Broell |

OTHER PUBLICATIONS

U.S. Appl. No. 12/299,217, filed Dec. 27, 2011, U.S. Pat. No. 8,084,640, Broell et al.
U.S. Appl. No. 12/300,189, filed Dec. 25, 2012, U.S. Pat. No. 8,337,671, Broell et al.
U.S. Appl. No. 12/517,563, filed Jun. 4, 2009, 2010/0069666, Dirk Broell.
International Search Report dated Nov. 11, 2018 in PCT/EP2018/067357.
Written Opinion dated Nov. 11, 2018 in PCT/EP2018/067357.

* cited by examiner

PROCESS FOR CONTINUOUS DISSOLUTION OF A SOLID IN A REACTION MEDIUM

CROSS-REFERENCE TO RELATED APPLICATIONS

This application is a National Stage entry under § 371 of International Application No. PCT/EP2018/067357, now WO 2019/007786, filed on Jun. 28, 2018, and which claims the benefit of German Application No. 10 2017 211 435.5, filed on Jul. 5, 2017. The contents of each of these applications is hereby incorporated by reference in their entirety.

BACKGROUND OF THE INVENTION

Field of the Invention

The invention relates to a process for continuously dissolving a solid, in particular a poorly soluble solid, in a reaction medium.

Description of the Art

A fundamental problem in chemical process engineering is the addition of poorly soluble solids to a reaction medium. Classically, poorly soluble additives are dissolved in a suitable solvent in a separate reaction vessel (premixing vessel) and this solution is subsequently added to the actual reaction medium. For additives having particularly low solubility in the actual reaction medium this approach requires either a large volume of the premixing vessel and/or the use of an additional solvent in which the additive is readily soluble. However, both variants have disadvantages: Installation of a high-volume pre-mixing vessel requires additional expenditure and space. This is particularly problematic when existing plants are to be retrofitted with such a premixing vessel. By contrast the use of an additional solvent entails unwanted contamination of the actual reaction medium with the solvent and may necessitate complex and costly separation of the reaction product from the solvent.

These problems will now be elucidated using the production of methacrylic anhydride as an example. The production of methacrylic anhydride is effected by acid-catalyzed transanhydridization of acetic anhydride with methacrylic acid in a rectification column. Such a process is described in DE 3510035 A1 for example. DE 20 2006 060 162 A1 discloses that a polymerization inhibitor is added to avoid polymerization of the reaction products. The polymerization inhibitor may be added into the feed before the reaction region and/or directly into the rectification column. The polymerization inhibitor employed in the described process is preferably phenothiazine. However, phenothiazine is poorly soluble in the medium of the transanhydridization reaction so that typically a solution of phenothiazine in acetone produced in a separate container is introduced into the process, resulting in the above-mentioned disadvantages.

BRIEF SUMMARY OF THE INVENTION

It is an object of the present invention to provide an improved process for continuously dissolving a solid in a reaction medium which eschews the use of additional solvents and may be realized while eschewing a high-volume premixing vessel.

The invention provides a process for continuously dissolving a solid in a reaction medium comprising the steps of:
a. providing a liquid by withdrawal of a portion of the reaction medium from a first reaction vessel;
b. contacting the liquid provided in step a) with the solid in a second reaction vessel to form a solution of the solid, wherein the solid in the second reaction vessel is present in the form of a fixed bed which is traversed by the liquid; and
c. recycling the solution formed in step b) into the first reaction vessel.

DETAILED DESCRIPTION OF THE INVENTION

The process according to the invention has the advantage that to dissolve the solid no additional solvent need be introduced into the system but rather the solid is dissolved directly in a portion of the reaction medium. In addition the process may be configured to be continuous in that a portion of the reaction medium is withdrawn from the first reaction vessel and passed through the second reaction vessel continuously. Through suitable choice of the structure of the fixed bed and of the flow rate of the liquid traversing the fixed bed it can also be ensured that the solid is dissolved in sufficient concentration. Consequently, a high-volume premixing vessel may be eschewed. The volume of the second reaction vessel may accordingly be minimized.

The reaction medium is preferably a liquid or a mixture of gaseous and liquid phases. Gaseous constituents are optionally liquefied during the withdrawal in step a) to provide the liquid required for step b). The reaction medium may comprise one or more chemical components. It is preferable when the first reaction medium comprises at least one reactant and at least one product of a chemical reaction. In addition the reaction medium may comprise for example solvents, catalysts and auxiliaries.

The portion of the reaction medium withdrawn in step a) may have the same composition as the reaction medium or may differ in composition from the reaction medium. The latter is the case for example when the reaction medium comprises at least two chemical components and before and/or during the withdrawal in step a) is subjected to a separation process so that the withdrawn portion of the reaction medium has a different composition to the reaction medium. Before or during the withdrawal the reaction medium may be subjected to a filtration or distillation for example. In this way for example it is possible to use only one component of the reaction medium, for example only one particular reactant, for dissolving the solid. The component in which the solid has the highest solubility may be advantageously withdrawn here.

In one embodiment the first reaction container comprises a rectification column from which the withdrawal is effected. By withdrawal of a portion of the reaction medium at a particular point of the rectification column the composition of the portion of the reaction medium withdrawn in step a) may be determined. In this way it is possible for example to ensure that in step a) only a certain component of the reaction medium is withdrawn and used for dissolving the solid. Similarly, the solution of the solid in step c) may be recycled at a freely choosable point on the rectification column.

When using a rectification column it is also possible in step a) to withdraw a gaseous reaction medium or a mixture of liquid and gaseous reaction medium. In this case the reaction medium is preferably fully liquefied after withdrawal, for example via a condenser, to provide the liquid for the contacting with the solid in step b).

The solid is present in the second reaction vessel in the form of a fixed bed and is traversed by the liquid withdrawn in step a). The solubility of the solid may be easily adapted by a person skilled in the art through suitable choice of the temperature of the fixed bed, the flow rate and the geometry of the fixed bed. The liquid may traverse the fixed bed for example either from top to bottom (in the direction of gravity) or in the opposite direction. The flow direction may be chosen based on the particular application. For example it has proven advantageous for the liquid to traverse the fixed bed from bottom to top (counter to gravity) since traversal from above can result in compaction of the fixed bed and a severe pressure buildup. Traversal from bottom to top also has the advantage that on startup of the process the air present in the fixed bed is uniformly discharged upward. By contrast, traversal from top to bottom (in the direction of gravity) has the advantage that formation of a fluidized bed which can have a negative effect on the solubility of the solid is avoided.

In one embodiment the second reaction vessel comprises a filter housing comprising a bag filter in which the fixed bed is stored. In this embodiment the fixed bed is preferably traversed by the liquid from top to bottom.

In an alternative embodiment the second reaction vessel comprises a tube which is open on two sides and whose openings are closed with frits between which the fixed bed is stored. This facilitates uniform traversal of the fixed bed and also allows traversal from bottom to top without the fixed bed being discharged from the second reaction vessel.

In one embodiment the second reaction vessel comprises two or more separate fixed beds which are simultaneously or alternately traversed by the liquid. The fixed beds are preferably connected in parallel. In this way the continuous operation of the process may be maintained in case solid in a fixed bed requires replenishment.

The concentration of the solid in the solution may vary as a result of transitory disturbance variables or a change in the dissolution procedure over time. This is the case for example when the surface of the solid is altered by the dissolution procedure, the residence time of the liquid increases as a result of the increase in free volume in the second reaction vessel or the flow rate decreases as a result of the increase in free volume.

To counter this variation in solid concentration in one embodiment a portion of the liquid withdrawn in step a) may not be contacted with the solid but rather mixed with the solution formed in step b) and the thus obtained mixture recycled into the first reaction vessel. This may be realized by dividing the portion of the reaction medium withdrawn in step a) into two substreams of which only one is passed through the second reaction vessel and the other portion is passed by the second reaction vessel as a bypass stream and mixed with the solution formed in step b). The mixing ratio of bypass stream to solution may be freely chosen. This measure makes it possible to precisely adjust the concentration of the solid in the solution recycled into the first reaction vessel and to compensate for any concentration variations.

It is particularly advantageous when the contacting of the liquid with the fixed bed in step b) is effected such that the concentration of the solid in the solution reaches the saturation concentration. This may be achieved by suitable choice of the dissolution conditions, in particular of the temperature of the fixed bed, of the flow rate of the liquid and of the geometry of the fixed bed. In this way the concentration of the solution recycled into the first reaction vessel may be adjusted over the greatest possible range by dilution with a bypass stream.

In one embodiment respective pressure measurements are performed before and after the second reaction vessel. The pressure difference can be used to determine the fill level of the fixed bed. The pressure difference may then be used to adjust the mixing ratio of bypass stream to solution to compensate for the concentration variations elucidated above. In one embodiment respective pressure measurements are accordingly performed before and after the second reaction vessel and the mixing ratio of bypass stream to solution is adjusted according to the thus determined pressure difference.

It is preferable when the concentration of the solid in the solution obtained in step b) is measured continuously. The measurement is preferably effected by spectrometry, particularly preferably using a UV/VIS spectrometer. This measure facilitates in particular precise adjustment of the concentration of the solid in the solution in combination with the above-described bypass stream. The mixing ratio of bypass stream and solution may be adjusted according to the measured concentration. In one embodiment the concentration of the solid in the solution is accordingly measured continuously and the mixing ratio of bypass stream to solution adjusted according to the thus determined concentration.

The concentration measurement may be effected by withdrawing samples of the solution at regular intervals and analyzing them in a suitable analytical method. However it is preferable to employ a continuous flow process where the solution is passed through a suitable analytical instrument continuously. This may also be effected such that only a portion of the solution is passed through the analytical instrument and a second portion is passed by the analytical instrument in a bypass. It is particularly preferable when at least a portion of the solution is passed through a UV/VIS spectrometer before the solution is recycled into the first reaction vessel.

In a preferred embodiment the above-described process is used for continuous dissolution of a solid in a reaction medium for continuous production of unsaturated carboxylic anhydrides by transanhydridization. A corresponding production process is disclosed for example in DE 20 2006 060 162 A1 and DE 10 2006 029 320 B3.

The solid may be an additive for the production process, such as catalysts, precipitants, defoamers and in particular polymerization inhibitors. In this context a polymerization inhibitor is to be understood as meaning a compound which inhibits the polymerization of substances having a propensity for polymerization, for example unsaturated carboxylic acids/unsaturated carboxylic anhydrides. In a preferred embodiment the solid is a polymerization inhibitor which inhibits the polymerization of unsaturated carboxylic acids/unsaturated carboxylic anhydrides. Preferred polymerization inhibitors include inter alia octadecyl-3-(3,5-di-tertbutyl-4-hydroxyphenyl) propionate, phenothiazine, hydroquinone, hydroquinone monomethyl ether, 4-hydroxy-2,2,6,6-tetramethylpiperidinooxyl (TEMPOL), 2,4-dimethyl-6-tert-butylphenol, 2,6-di-tert-butylphenol, 2,6-di-tert-butyl-4-methylphenol, para-substituted phenylenediamines such as for example N,N'-diphenyl-p-phenylenediamine, 1,4-benzoquinone, 2,6-di-tert-butyl-alpha-(dimethylamino)-p-cresol, 2,5-di-tert-butylhydroquinone or mixtures of two or more of these stabilizers. In a particularly preferred embodiment the solid is phenothiazine.

In one embodiment the reaction medium comprises at least one unsaturated carboxylic anhydride of general formula (I) R—C(O)—O—C(O)—R in which R represents an unsaturated organic radical having 2 to 12 carbon atoms, at least one unsaturated carboxylic acid of general formula (II) R—COOH in which R is as defined above, at least one aliphatic carboxylic anhydride and at least one corresponding aliphatic carboxylic acid. The organic radical R may optionally be substituted with any desired number of halogen atoms or cyano groups.

Unsaturated carboxylic acids of formula (II) suitable for the process according to the invention have an unsaturated organic radical having 2 to 12, preferably 2 to 6, particularly preferably 2 to 4, carbon atoms. Suitable alkenyl groups are the vinyl, allyl, 2-methyl-2-propene, 2-butenyl, 2-pentenyl, 2-decenyl, 1-undecenyl and 9,12-octadecadienyl groups. The vinyl and allyl groups are particularly preferred.

The particularly preferred unsaturated carboxylic acids include inter alia (meth)acrylic acids. The term (meth) acrylic acids is known in the art and is to be understood as meaning not only acrylic acid and methacrylic acid but also derivatives of these acids. These derivatives include inter alia β-methylacrylic acid (butenoic acid, crotonic acid), α,β-dimethylacrylic acid, β-ethylacrylic acid, α-chloroacrylic acid, α-cyanoacrylic acid, 1-(trifluoromethyl)acrylic acid and also beta, β-dimethylacrylic acid. Acrylic acid (propenoic acid) and methacrylic acid (2-methylpropenoic acid) are preferred.

Suitable aliphatic carboxylic anhydrides for the inventive process are likewise known to those skilled in the art. Preferred compounds have general formula (III) R'—C(O)—O—C(O)—R', in which R' represents a C1 to C4-alkyl radical.

It is preferable to employ acetic anhydride.

The corresponding aliphatic carboxylic acid is preferably an aliphatic carboxylic acid having 1 to 4 carbon atoms. Acetic acid is particularly preferred.

It is particularly preferable when the reaction medium comprises (meth)acrylic acid, (meth)acrylic anhydride, acetic acid, acetic anhydride and the mixed anhydride acetyl methacrylate.

The reaction medium may also comprise further components, for example solvents and catalysts.

In this embodiment the first reaction vessel preferably comprises a rectification column. In addition, the reaction vessel may comprise a region, hereinbelow reaction region or reactor, in which preferably at least one catalyst is provided. This reactor may be inside and/or outside the rectification column. However, the reactor is preferably arranged outside the rectification column in a separate region. The reaction medium is continuously recirculated in a recycle stream between the reactor and the rectification column. The withdrawal of a portion of the reaction medium in step a) may be effected from the reactor and/or the rectification column. The withdrawal is preferably effected from the rectification column.

The process according to the invention may employ for example a rectification column having an upper, middle and lower region having 5 to 15 separating stages in each of the upper, middle and lower regions. It is preferable when the number of the separating stages in the upper region is 10 to 15 and in the middle and lower regions is 8 to 13. In the present invention the number of separating stages is to be understood as meaning the number of trays in a tray column multiplied by the tray efficiency or the number of theoretical separating stages in the case of a structured packing column or a column comprising random packings.

Examples of trays in a rectification column comprising trays include bubble cap trays, sieve trays, tunnel trays, valve trays, slit trays, sieve slit trays, sieve bubble cap trays, nozzle trays, centrifugal trays, examples of random packings in a rectification column comprising random packings include Raschig rings, Lessing rings, Pall rings, Ber saddles, Intalox saddles, and examples of structured packings in a rectification column comprising structured packings include the Mellapak (Sulzer), Rombopak (Kahni) and Montz-Pak (Montz) types and structured packings comprising catalyst bags, for example Katapak (Sulzer). A rectification column comprising combinations of regions of trays, of regions of random packings and/or of regions of structured packings may likewise be employed. It is preferable to employ a rectification column comprising random packings and/or structured packings for the 3 regions. The rectification column may be produced from any material suitable therefor. These include inter alia stainless steel and inert materials.

In one embodiment a boiling oil has been initially charged into the bottom of the rectification column. As the boiling oil for the process according to the invention a high-boiling, inert substance with long-term thermal stability and a boiling point higher than the boiling points of the components involved in the reaction is employed in order to ensure distillative removal of the formed acid anhydride without polymerization. However, the boiling point of the boiling oil should not be so high as to reduce the thermal stress on the acid anhydride formed. Generally the boiling point of the boiling oil at standard pressure (1013 mbar) is 200° C. to 400° C., in particular 240° C. to 290° C. Suitable boiling oils are inter alia longer-chained unbranched paraffins having 12 to 20 carbon atoms, aromatic compounds such as diphyl (eutectic mixture of 75% biphenyl oxide and 25% biphenyl), alkyl-substituted phenols or naphthalene compounds, sulfolane (tetrahydrothiophene-1,1-dioxide) or mixtures thereof. Particularly preferably employed are 2,6-di-tert-butyl-para-cresol, 2,6-di-tert-butyl-phenol, sulfolane, diphyl or mixtures thereof, very particularly preferably sulfolane.

The reaction medium is preferably at a temperature in the range from 30° C. to 120° C., particularly preferably 40° C. to 100° C., in particular 50° C. to 80° C. The temperature is dependent on the established system pressure. In one arrangement of the reactor inside the column the reaction is preferably performed in the pressure range of 5 to 100 mbar (absolute), in particular at 10 to 50 mbar (absolute) and particularly preferably at 20 to 40 mbar (absolute). If the reactor is located outside the column, pressure and temperature conditions distinct from those in the column may be chosen therein. This has the advantage that the reaction parameters of the reactor may be adjusted independently of the operating conditions in the column. The reaction time of the transanhydridization depends on the reaction temperature; the residence time in the reactor for a single pass is preferably 0.5 to 15 minutes and particularly preferably 1 to 5 minutes. In the production of (meth)acrylic anhydride from acetic anhydride and (meth)acrylic acid the temperature of the reaction medium is preferably 40° C. to 100° C., particularly preferably 50° C. to 90° C. and very particularly preferably 70° C. to 85° C.

It is preferable when heterogeneous catalysts are employed in the reaction region. Particularly suitable heterogeneous catalysts are acidic fixed bed catalysts, in particular acidic ion exchangers. Particularly suitable ion exchangers include in particular cation exchange resins such as styrene-divinyl benzene polymers containing sulfonic acid groups. Suitable cation exchange resins are commercially available from Rohm&Haas under the trade name Ambertyst®, from Dow under the trade name Dowex® and from Lanxess under the trade name Lewatit®. The catalyst amount in L is preferably ¹⁄₁₀ to 2 times, particularly preferably ⅕ to ½, of the amount of newly formed unsaturated carboxylic anhydrde to be produced in L/h.

In one embodiment the liquid to dissolve the solid is withdrawn at the top of the rectification column. In this embodiment the portion of the reaction medium withdrawn in step a) is preferably passed through a condenser to fully condense gaseous constituents. This variant is particularly suitable for dissolving a polymerization inhibitor, in particular phenothiazine.

It is preferable here when the liquid withdrawn in step a) is substantially the at least one aliphatic carboxylic acid, particularly preferably acetic acid. In one embodiment the portion of the reaction medium withdrawn in step a) consists of aliphatic carboxylic acids to an extent of at least 90% by weight, preferably at least 95% by weight, particularly preferably at least 99% by weight. It is particularly preferable when the portion of the reaction medium withdrawn in step a) consists of acetic acid to an extent of at least 90% by weight, preferably at least 95% by weight, particularly preferably at least 99% by weight.

The temperature of the liquid withdrawn in step a) is preferably set to a range from 10° C. to 80° C., preferably 10° C. to 60° C., particularly preferably 15° C. to 30° C.

The pressure of the liquid withdrawn in step a) is preferably set to a range from 1 to 10 bar, preferably 2 to 7 bar, particularly preferably 3 to 6 bar.

The temperature of the fixed bed in step b) is preferably set to a range from 10° C. to 80° C., preferably 10° C. to 60° C., particularly preferably 15° C. to 30° C.

In the case where the solid is phenothiazine and the liquid withdrawn in step a) is substantially an aliphatic carboxylic acid, preferably acetic acid, the process according to the invention can continuously generate a solution having a phenothiazine concentration of 1% to 3% by weight. If in addition a bypass stream for diluting the phenoxythiazine solution is employed a diluted solution having a concentration of 900 to 1000 ppm may be generated.

The solution may in step c) be recycled either into the rectification column and/or into the optionally present reactor. If the solid is a polymerization inhibitor the recycling is preferably effected into the top of the rectification column.

Figure 1:
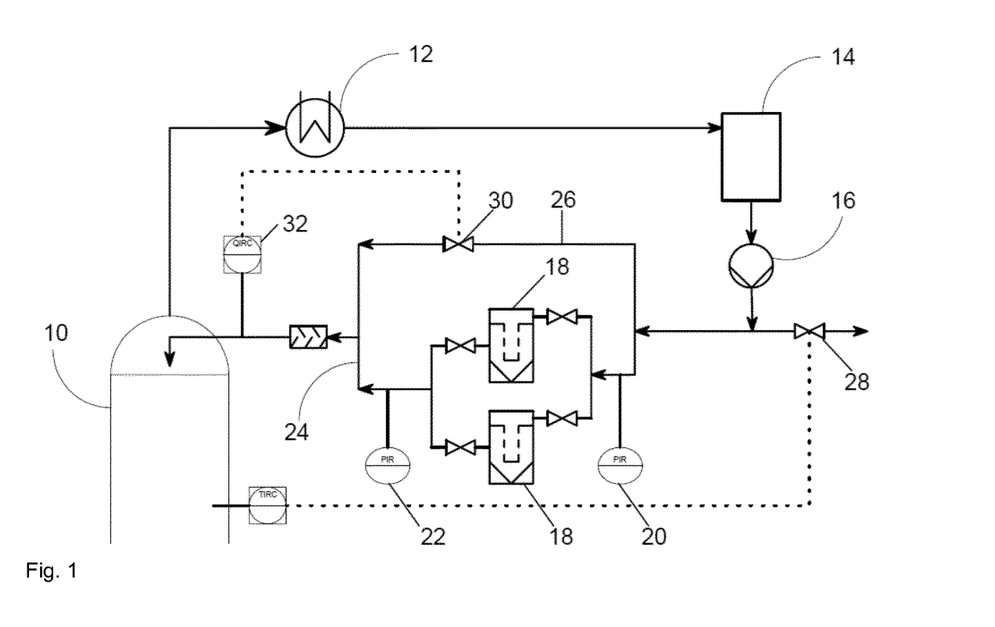
FIG. 1 Schematic representation of a preferred embodiment of the process according to the invention.

The process according to the invention is illustrated by way of example with reference to FIG. 1. In a rectification column (10) a reaction medium is initially charged. At the top of the rectification column (10) a portion of the reaction medium is withdrawn and passed through a condenser (12) to fully condense gaseous constituents of the reaction medium. The liquid is passed through an optional buffering vessel (14) and a pump (16). The pump allows the liquid pressure to be adjusted. A portion of the liquid is passed through at least one of two reaction vessels (18) connected in parallel and therein contacted with a solid to form a solution of the solid. The solid is present in the reaction vessels (18) in the form of a fixed bed. Pressure-measuring means (20, 22) may be installed before and after the reaction vessels (18). The solution is sent on via the conduit (24). A second portion of the liquid is passed by the reaction vessels (18) in a bypass stream (26). A further portion of the liquid may be discharged via the conduit (28). The bypass stream (26) is mixed with the solution in conduit (24). The mixing ratio may be adjusted by controlling the valve (30). The mixture of bypass stream and solution is passed through a UV/VIS detector which can determine the concentration of the solid in the mixture. The control of the valve (30) may be determined according to the concentration determined by the UV/VIS detector (32). After passing through the UV/VIS detector (32) the mixture returns to the top of the rectification column (10).

DESCRIPTION OF THE FIGURES

FIG. 1 Schematic representation of a preferred embodiment of the process according to the invention.

Figure 2:
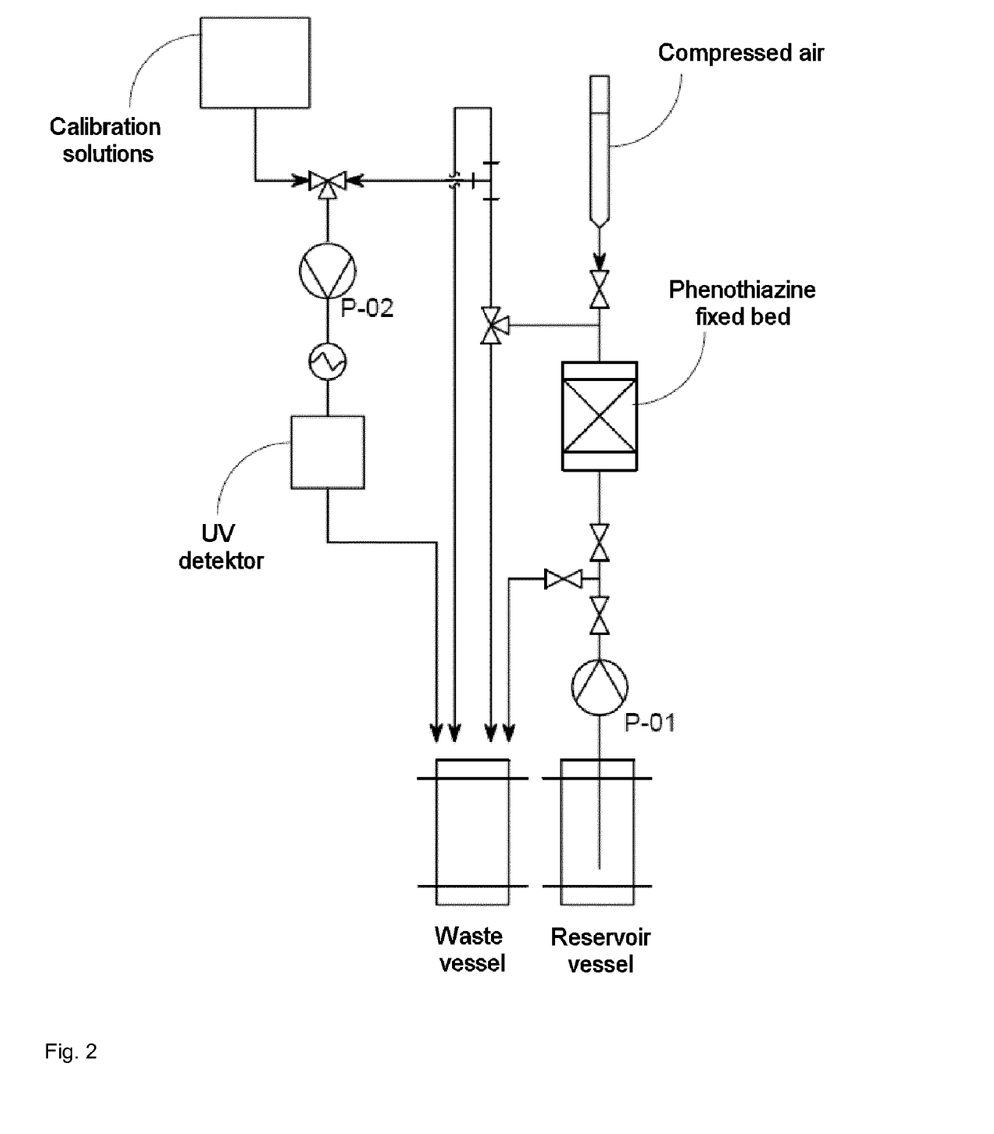
FIG. 2 Test setup for dissolution of phenothiazine in acetic acid.

FIG. 2 Test setup for dissolution of phenothiazine in acetic acid.

Figure 3:
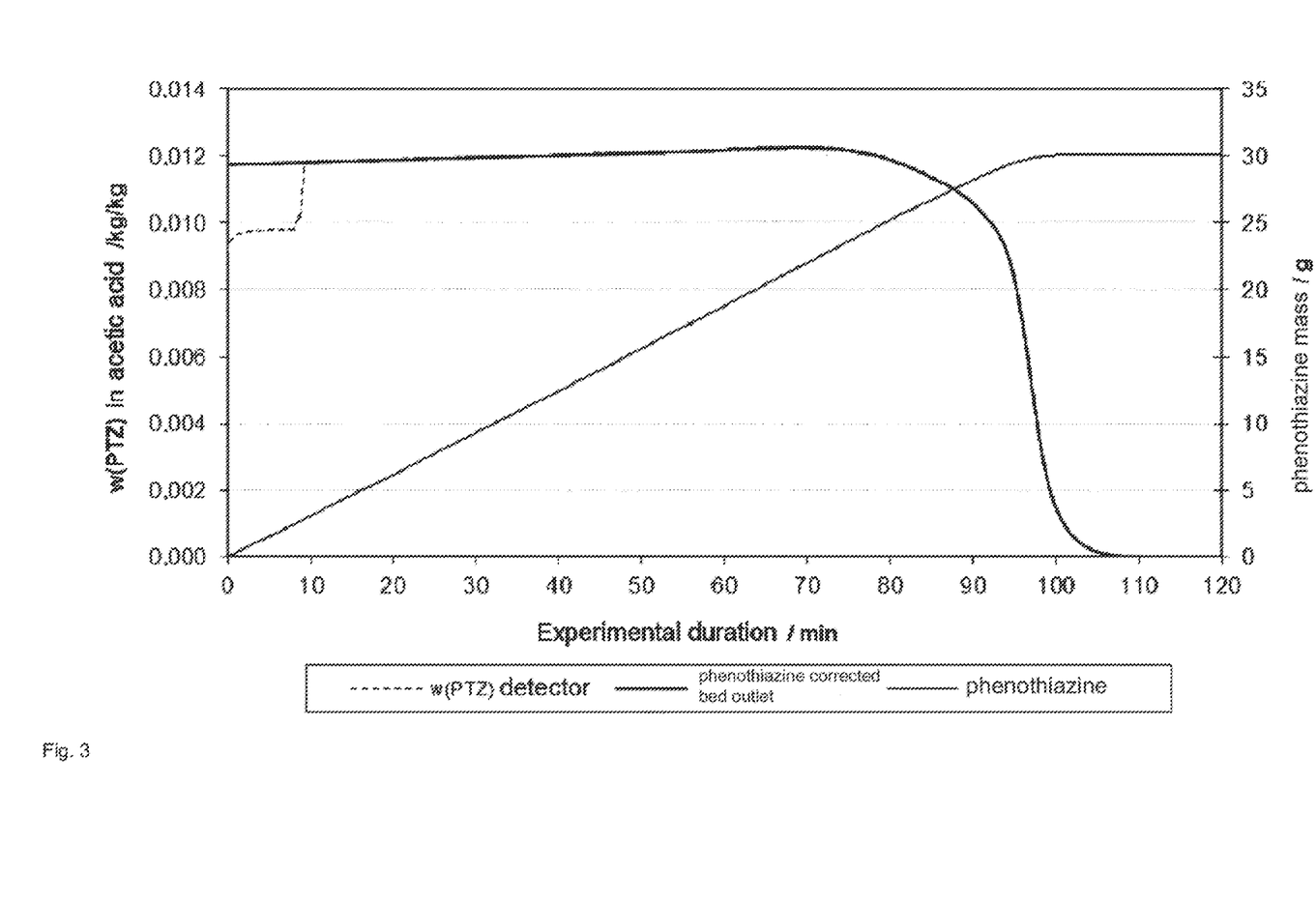
FIG. 3 Phenothiazine concentration profile of experiment 1.

FIG. 3 Phenothiazine concentration profile of experiment 1.

Figure 4:
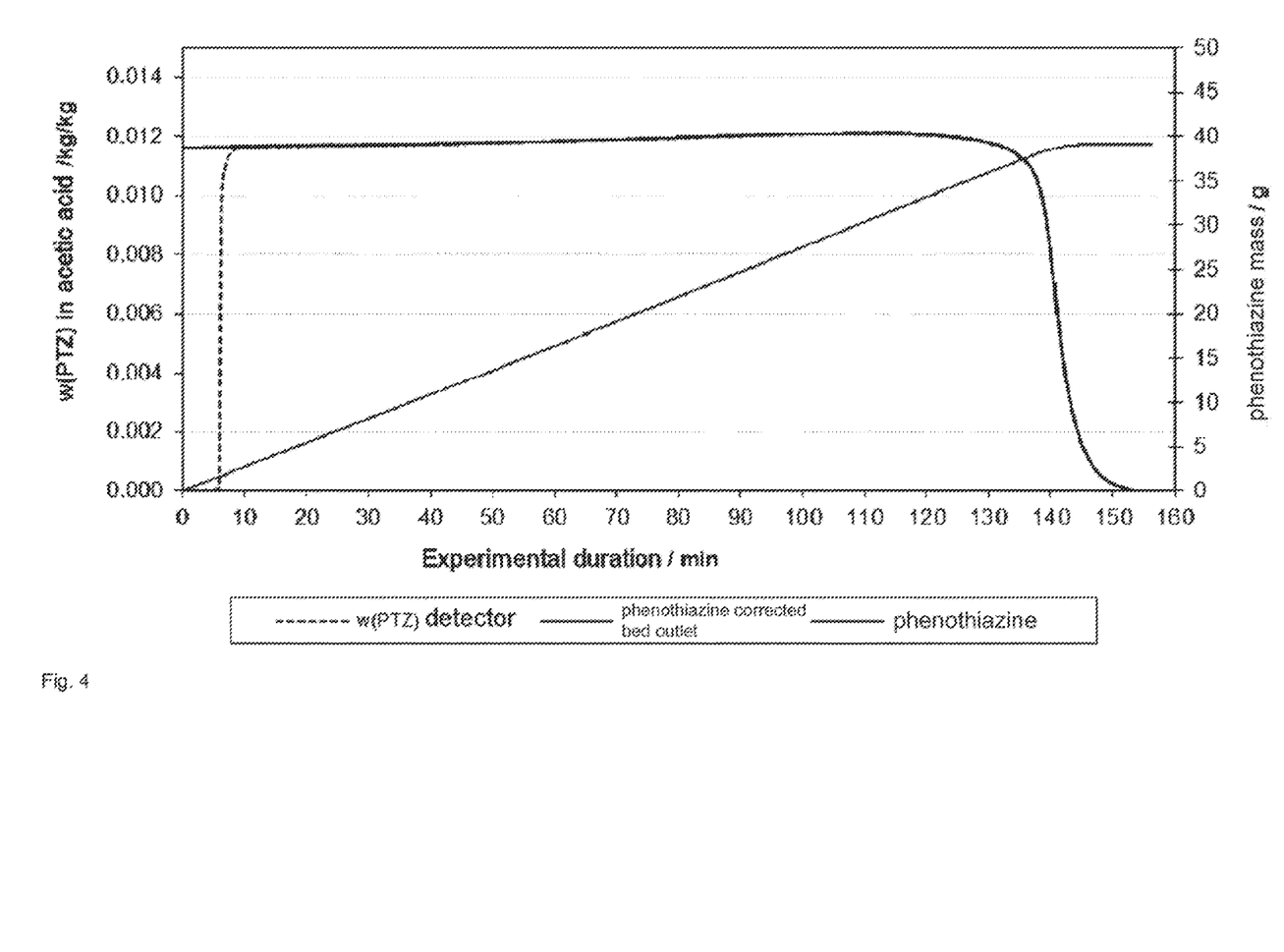
FIG. 4 Phenothiazine concentration profile of experiment 2.

FIG. 4 Phenothiazine concentration profile of experiment 2.

LIST OF REFERENCE SYMBOLS

10 Rectification column
12 Condenser
14 Buffer vessel
16 Pump
18 Reaction vessel comprising fixed bed
20,22 pressure-measuring means
24 Conduit
26 Bypass conduit
28 Conduit
30 Valve
32 UV/VIS detector

EXAMPLE

The dissolution of phenothiazine in acetic acid according to the process according to the invention was investigated by experiment. FIG. 2 illustrates the relevant experimental setup.

A phenothiazine fixed bed is placed in a temperature-controllable chromatography column (Götec-Labor GmbH, Superformance 300-16, length 300 mm, internal diameter 16 mm, double-walled for thermostatting, 20 μm type F filter frit). Pump P-01 conveys acetic acid from the reservoir vessel through the fixed bed temperature-controlled to 20° C. into a waste vessel. Pump P-02 diverts a sample stream to the UV detector. The phenothiazine concentration is determined by absorption measurement at 390 nm. The detector is previously calibrated with a phenothiazine solution of known concentration.

A first experiment was performed with a flow rate of 12.4 cm/min at a volume flow of 25.0 ml/min. FIG. 3 shows the phenothiazine concentration profile (solid curve beginning at a concentration between 0.010 and 0.012 kg/kg) versus experimental duration. The measured detector extinction (dashed) periodically deviates from the concentration at the bed outlet since to protect the measuring cell from solids particles the solution was not passed through the detector upon startup. In the further course of the experiment calibration solutions were passed through the detector as a control. The "corrected bed outlet concentration" (solid curve beginning at a concentration of 0.000) was calculated over the experimental duration via linear interpolation and extrapolation. As a control parameter, on the secondary axis the phenothiazine mass was summed from the concentration profile.

The solid was subjected to flow from below and until the 90th minute of the experiment lay at the bottom of the chromatography column in a slightly loosened state. The supernatant space underwent increasing enlargement due to the dissolution of phenothiazine and a backmixing space was thus formed. Slightly turbulent streaks in the free volume and also the tailing of the concentration profile at the end of the experiment indicate the presence of backmixing. A slight increase in the phenothiazine concentration over the course of the experiment, attributable to increasing residence time as a result of the continual enlargement of the free space, was observed.

A second experiment was based on a flow rate of 11.0 cm/min. The starting weight of phenothiazine was increased to 40 g on account of better utilization of the column volume. FIG. 4 shows the phenothiazine concentration profile of experiment 2.

The following table shows a summary of the experimental parameters. The table also shows a production scale projection of the uptime of the phenothiazine fixed bed at an assumed fixed bed height of 70 cm and a throughput per unit area of about 11.7 ml/(min cm$^2$). The phenothiazine concentration only fell below the minimum required concentration of 1% by weight after 343 minutes (5.7 h) on the production scale.

| Parameter | Unit | Experiment 1 | Experiment 2 |
|---|---|---|---|
| Starting weight of phenothiazine | g | 30.4 | 41.0 |
| Bed height | cm | 18.8 | 27.0 |
| Bed volume *) | g/cm | 0.80 | 0.76 |
| Thermostatted temperature | ° C. | 20.0 | 20.0 |
| Volume flow | ml/min | 25.0 | 22.2 |
| Flow rate (empty) | cm/min | 12.4 | 11.0 |
| Throughput per unit area | ml/(min cm$^2$) | 12.4 | 11.0 |
| Max conc (phenothiazine) | % by wt. | 1.23 | 1.22 |
| Conc (phenothiazine) <1.0% by weight | min | 92 | 138 |
| Specific time to fall below **) | min/cm | 4.9 | 5.1 |
| Production scale bed height | cm | 70 | 70 |
| Time to fall below 1.0% by weight | min | 343 | 358 |

*) Measured bulk density 0.74 g/cm$^3$
**) Time taken to fall below concentration of 1.0% by weight at 20° C. and a throughput per unit area of about 11.7 ml/(min cm$^2$) (±0.7).

Calculation of the phenothiazine concentration in the acetic acid reflux of the rectification column on production scale was based on the concentration profile from experiment 2 (FIG. 4). Uptime increases according to the initial bed heights of 27 cm in the experimental fixed bed to the maximum bed height of 70 cm on the production scale (using sack filters) by a factor of 2.6 (=70/27). When the correspondingly concentrated phenothiazine solution is mixed in a 1:10 ratio with pure acetic acid (bypass stream) a reflux concentration to the rectification column of between 880 and 925 ppm of phenothiazine results.

These experiments show that the saturation concentration of phenothiazine in acetic acid is established over the entire experimental duration and thus confirm that the process according to the invention may be used to introduce phenothiazine into a reaction medium for the production of unsaturated carboxylic anhydrides.

The invention claimed is:

1. A process for continuous dissolution of a solid in a reaction medium, comprising:
    a) withdrawing a liquid, which is a portion of the reaction medium, from a first reaction vessel;
    b) contacting the liquid withdrawn from the first reaction vessel in a) with a solid in a second reaction vessel to form a solution of the solid, wherein the solid in the second reaction vessel is present in a form of a fixed bed which is traversed by the liquid; and
    c) recycling the solution formed in b) into the first reaction vessel.

2. The process according to claim 1, wherein the reaction medium comprises a liquid phase or a mixture of gaseous and liquid phases, and gaseous constituents are liquefied during the withdrawal in a).

3. The process according to claim 1, wherein the reaction medium comprises at least two chemical components, and before or during the withdrawal in a), the reaction medium is subjected to a separation process so that the portion of the reaction medium withdrawn in a) has a different composition to the reaction medium.

4. The process according to claim 1, wherein the first reaction vessel comprises a rectification column from which the withdrawal in a) is effected.

5. The process according to claim 1, wherein the liquid traverses the fixed bed from bottom to top in b).

6. The process according to claim 1, wherein the second reaction vessel comprises two or more fixed beds connected in parallel.

7. The process according to claim 1, wherein the portion of the reaction medium withdrawn in a) is divided into two substreams, of which only a first of the two substreams is passed through the second reaction vessel and a second of the two substreams is passed by the second reaction vessel as a bypass stream and mixed with the solution formed in b).

8. The process according to claim 1, wherein respective pressure measurements are performed before and after the second reaction vessel and a thus determined pressure difference is used to determine a fill level of the fixed bed.

9. The process according to claim 1, wherein the concentration of the solid in the solution obtained in b) is measured continuously by a UV/VIS spectrometer.

10. The process according to claim 1, wherein the reaction medium comprises:
    at least one unsaturated carboxylic anhydride of general formula R—C(O)—O—C(O)—R, in which R represents an unsaturated organic radical having 2 to 12 carbon atoms,
    at least one unsaturated carboxylic acid of general formula R—COOH in which R is as defined above,
    at least one aliphatic carboxylic anhydride, and
    at least one corresponding aliphatic carboxylic acid,
    wherein R is optionally substituted with any desired number of halogen atoms or cyano groups.

11. The process according to claim 10, wherein
    the reaction medium comprises (meth)acrylic acid, (meth)acrylic anhydride, acetic acid, and acetic anhydride.

12. The process according to claim 10, wherein the solid is phenothiazine.

13. The process according to claim 10, wherein the first reaction vessel comprises a rectification column, and the withdrawal in a) is effected in a top of the rectification column.

14. The process according to claim 10, wherein the portion of the reaction medium withdrawn in a) comprises aliphatic carboxylic acids to an extent of at least 90% by weight.

15. The process according to claim 10, wherein a temperature of the fixed bed is set to a range from 10° C. to 80° C.

16. A continuous dissolution system, comprising:
a first reaction vessel comprising a reaction medium, and
a second reaction vessel comprising a solid,
wherein a portion of the reaction medium is withdrawn from the first reaction vessel and introduced to the second reaction vessel, thereby contacting the solid to form a solution of the solid,
wherein the solution is recycled back to the first reaction vessel, and
wherein the solid is present in a form of a fixed bed.

17. The system according to claim 16, wherein the reaction medium comprises (meth)acrylic acid, (meth)acrylic anhydride, acetic acid, and acetic anhydride, and wherein the solid is phenothiazine.

\* \* \* \* \*